(12) United States Patent  
Kobayashi

(10) Patent No.: US 11,197,603 B2
(45) Date of Patent: Dec. 14, 2021

(54) ENDOSCOPE APPARATUS

(71) Applicant: Sony Olympus Medical Solutions Inc., Tokyo (JP)

(72) Inventor: Motoaki Kobayashi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 137 days.

(21) Appl. No.: 16/481,068

(22) PCT Filed: Oct. 27, 2017

(86) PCT No.: PCT/JP2017/038985
§ 371 (c)(1),
(2) Date: Jul. 26, 2019

(87) PCT Pub. No.: WO2018/163500
PCT Pub. Date: Sep. 13, 2018

(65) Prior Publication Data
US 2019/0387964 A1 Dec. 26, 2019

(30) Foreign Application Priority Data

Mar. 10, 2017 (JP) .............................. JP2017-046604

(51) Int. Cl.
*A61B 1/06* (2006.01)
*A61B 1/00* (2006.01)
*A61B 1/045* (2006.01)

(52) U.S. Cl.
CPC ........ *A61B 1/0653* (2013.01); *A61B 1/00163* (2013.01); *A61B 1/045* (2013.01); *A61B 1/0638* (2013.01); *A61B 1/0661* (2013.01)

(58) Field of Classification Search
CPC ... A61B 1/0653; A61B 1/00163; A61B 1/045; A61B 1/0638
See application file for complete search history.

(56) References Cited

U.S. PATENT DOCUMENTS 5,099,317 A * 3/1992 Takemura ............ H04N 5/2258
348/264
2003/0135092 A1* 7/2003 Cline ................... A61B 1/0638
600/160

(Continued)

FOREIGN PATENT DOCUMENTS

CN 102036599 A 4/2011
CN 104066367 A 9/2014

(Continued)

OTHER PUBLICATIONS

US 6,692,429 B1, 02/2004, Katsuichi et al. (withdrawn)

(Continued)

*Primary Examiner* — Alexandra L Newton
*Assistant Examiner* — Jae Woo
(74) *Attorney, Agent, or Firm* — Xsensus, LLP

(57) ABSTRACT

An endoscope apparatus according to the present invention includes: a light source device configured to continuously emit first light of a first wavelength band, and sequentially emit second light of plural second wavelength bands different from the first wavelength band and different from each other; and an imaging device including: a spectroscopic unit configured to spectrally separate light from a subject, the light being due to illumination light emitted by the light source device, into light of the first wavelength band and light of the second wavelength bands; a first imaging element configured to generate a first image signal by receiving and photoelectrically convert the light of the first wavelength band spectrally separated by the spectroscopic unit; and a second imaging element configured to generate a second image signal by respectively receiving and photoelectrically converting the light of the second wavelength bands spectrally separated by the spectroscopic means.

12 Claims, 8 Drawing Sheets

(56) References Cited

U.S. PATENT DOCUMENTS

| | | | | |
|---|---|---|---|---|
| 2004/0186351 A1* | 9/2004 | Imaizumi | ............ | A61B 5/0071 |
| | | | | 600/160 |
| 2008/0055450 A1* | 3/2008 | Wada | .................... | H04N 9/045 |
| | | | | 348/311 |
| 2014/0160260 A1* | 6/2014 | Blanquart | ............ | H04N 5/2256 |
| | | | | 348/68 |
| 2014/0316279 A1* | 10/2014 | Morishita | ............ | A61B 1/0638 |
| | | | | 600/476 |
| 2015/0173624 A1 | 6/2015 | Friedman | | |
| 2015/0289764 A1* | 10/2015 | Tamura | ................ | A61B 5/0084 |
| | | | | 600/476 |
| 2016/0100763 A1* | 4/2016 | Fengler | ................ | A61B 5/0086 |
| | | | | 600/473 |
| 2019/0387964 A1* | 12/2019 | Kobayashi | ........... | A61B 1/0638 |

FOREIGN PATENT DOCUMENTS

| | | |
|---|---|---|
| JP | 2007-235877 A | 9/2007 |
| JP | 2011-528918 A | 12/2011 |
| JP | 2017-131559 A | 8/2017 |
| WO | 2014/037979 A1 | 3/2014 |
| WO | 2016/006266 A1 | 1/2016 |
| WO | 2016/147435 A1 | 9/2016 |

OTHER PUBLICATIONS

Extended European Search Report dated Feb. 4, 2020 in European Application No. 17899999.1-1122.
International Search Report and Written Opinion dated Jan. 16, 2018 for PCT/JP2017/038985 filed on Oct. 27, 2017, 9 pages including English Translation of the International Search Report.

\* cited by examiner

ENDOSCOPE APPARATUS

CROSS-REFERENCE TO RELATED APPLICATIONS

The present application is based on PCT filing PCT/JP2017/038985, filed Oct. 27, 2017, which claims priority to JP 2017-046604, filed Mar. 10, 2017, the entire contents of each are incorporated herein by reference.

TECHNICAL FIELD

The present invention relates to an endoscope apparatus.

BACKGROUND ART

In medical image acquisition systems where images of subjects are captured by use of imaging elements for observation of the subjects, increase in definition of the captured images has been demanded conventionally for acquisition of more elaborate observation images. Known as an imaging device that enables acquisition of a captured image high in definition is, for example, an imaging device including plural imaging elements (see, for example, Patent Literature 1). The imaging device disclosed in Patent Literature 1 includes: a color separation prism, which is formed of plural prisms respectively provided with dichroic films that reflect or transmit light of wavelength bands different from one another, and which spectrally separates observation light into four wavelength bands respectively through the dichroic films; and four imaging elements, which capture images by receiving the observation light of the respective wavelength bands spectrally separated by the color separation prism; and in this imaging device: relatively to a reference that is pixels of one of the imaging elements, pixel positions of the remaining three imaging elements are displaced, for multiple pixels to be realized; and thereby high definition is realized.

CITATION LIST

Patent Literature

Patent Literature 1: Japanese Laid-open Patent Publication No. 2007-235877

DISCLOSURE OF INVENTION

Technical Problem

However, the imaging device disclosed in Patent Literature 1 has a problem that the imaging device is increased in size and weight due to the provision of the color separation prism therein. In addition, there is a problem that from transmission of the observation light through the first incoming surface of the color separation prism to transmission of the observation light through the last outgoing surface of the color separation prism, transmission and reflection of the observation light are repeated for a plural number of times with respect to surfaces of the plural prisms including the dichroic films, and thus the observation light is attenuated and a high quality captured image is unable to be acquired.

If an image of a quality that is about the same as that by the four imaging elements is attempted to be acquired by a single imaging element for an imaging device to be downsized, there is a need for the imaging element to separately receive light of wavelength bands of red (R), green (G), and blue (B) color components and to generate electric signals of these color components. With this configuration, imaging processing needs to be performed three times for a single image to be generated, and the frame rate is thus decreased. On the other hand, if imaging is performed with the frame rate maintained, the exposure time for imaging processing of one time is shortened, and the quality of the image is thus affected.

The present invention has been made in view of the above, and an object thereof is to provide an endoscope apparatus that enables acquisition of a high quality observation image while enabling prevention of increase in size and weight of the endoscope apparatus.

Solution to Problem

To solve the above-described problem and achieve the object, an endoscope apparatus according to the present invention includes: a light source device configured to continuously emit first light of a first wavelength band, and sequentially emit second light of plural second wavelength bands different from the first wavelength band and different from each other; and an imaging device including: a spectroscopic unit configured to spectrally separate light from a subject, the light arising from illumination light emitted by the light source device, into light of the first wavelength band and light of the second wavelength bands; a first imaging element configured to generate a first image signal by receiving and photoelectrically converting the light of the first wavelength band spectrally separated by the spectroscopic unit; and a second imaging element configured to generate a second image signal by respectively receiving and photoelectrically converting the light of the second wavelength bands spectrally separated by the spectroscopic unit.

Moreover, in the above-described endoscope apparatus according to the present invention, the light source device continuously emits light of a green wavelength band that is the first wavelength band, and sequentially emits light of a red wavelength band and light of a blue wavelength band, the red wavelength band and blue wavelength band being the second wavelength bands, and the first and second imaging elements generate the first and second image signals in synchronization with emission time periods of the first and second light by the light source device.

Moreover, in the above-described endoscope apparatus according to the present invention, the light source device enables switch-over between: normal illumination where, in a frame reading time period for reading of a signal corresponding to one frame, the light of the green wavelength band is continuously emitted and the light of the red wavelength band and the light of the blue wavelength band are sequentially emitted; and narrow band illumination where, in the frame reading time period, light of a green narrow band is emitted and light of a blue narrow band is also emitted.

Moreover, in the above-described endoscope apparatus according to the present invention, in a frame reading time period for reading of a signal corresponding to one frame, the light source device continuously emits the light of the green wavelength band and sequentially emits the light of the red wavelength band, the light of the blue wavelength band, and near infra-red light.

Moreover, the above-described endoscope apparatus according to the present invention, further includes a control device including: a control unit configured to control operation of the first and second imaging elements and control a wavelength band of light emitted by the light source device and emission timings; and an image generating unit configured to generate an image based on an electric signal generated by the first and second imaging elements.

Moreover, in the above-described endoscope apparatus according to the present invention, the first and second imaging elements are imaging elements having sensitivity to the first light and second light.

Advantageous Effects of Invention

The present invention has an effect of enabling acquisition of a high quality observation image while enabling prevention of increase in apparatus size and weight.

BEST MODE FOR CARRYING OUT THE INVENTION

Described hereinafter are modes for implementation of the present invention (hereinafter, referred to as "embodiments"). With respect to the embodiments, medical endoscope apparatuses for capturing and displaying in-vivo images of subjects, such as patients, will be described as examples of an endoscope apparatus according to the present invention. Furthermore, this invention is not limited by these embodiments. Moreover, any portions that are same will be assigned with the same reference sign throughout the drawings.

First Embodiment

Figure 1:
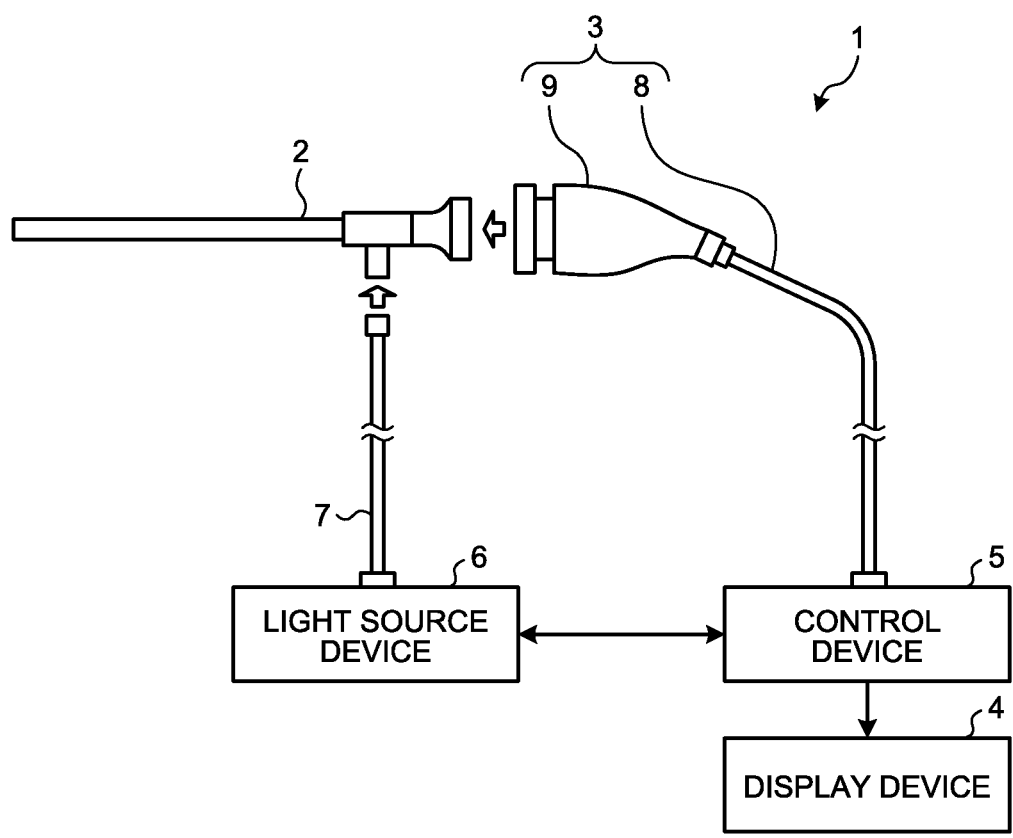
FIG. 1 is a diagram illustrating a schematic configuration of an endoscope apparatus according to a first embodiment of the present invention.

FIG. 1 is a diagram illustrating a schematic configuration of an endoscope apparatus 1 according to a first embodiment of the present invention. The endoscope apparatus 1 is an apparatus, which is used in the medical field and is for observation of a subject inside a target to be observed (in a living body), such as a human. This endoscope apparatus 1 includes, as illustrated in FIG. 1, an endoscope 2, an imaging device 3, a display device 4, a control device 5 (an image processing device), and a light source device 6. The endoscope apparatus is formed of at least the imaging device 3 and the light source device 6. According to this first embodiment, the endoscope apparatus is formed of the endoscope 2, the imaging device 3, the control device 5, and the light source device 6.

One end of a light guide 7 is connected to the endoscope 2, and the light source device 6 supplies white illumination light for illuminating the interior of the living body, to the one end of the light guide 7. The one end of the light guide 7 is attachably and detachably connected to the light source device 6, and the other end of the light guide 7 is attachably and detachably connected to the endoscope 2. The light guide 7 supplies the light supplied from the light source device 6 to the endoscope 2, by transmitting the light from the one end to the other end.

The imaging device 3 captures a subject image from the endoscope 2 that has acquired light from the subject, the light arising from the illumination light emitted from the light source device 6, and outputs a result of the image capturing. This imaging device 3 includes, as illustrated in FIG. 1, a transmission cable 8 that is a signal transmitting unit, and a camera head 9. According to this first embodiment, the transmission cable 8 and the camera head 9 form a medical imaging device.

The endoscope 2 is rigid, has an elongated shape, and is inserted into the living body. Provided inside this endoscope 2 is an optical system, which is formed by use of one or plural lenses and condenses a subject image. The endoscope 2 outputs the light supplied via the light guide 7, from a distal end of the endoscope 2, and irradiates the interior of the living body with the output light. The light (the subject image) emitted into the living body is condensed by the optical system (a lens unit 91 described later) in the endoscope 2.

The camera head 9 is attachably and detachably connected to a proximal end of the endoscope 2. Under control by the control device 5, the camera head 9 captures the subject image condensed in the endoscope 2, and outputs an imaging signal acquired by the image capturing. A detailed configuration of the camera head 9 will be described later.

The transmission cable 8 has one end attachably and detachably connected to the control device 5 via a connector, and another end attachably and detachably connected to the camera head 9 via a connector. Specifically, the transmission cable 8 is a cable having plural electric wirings (not illustrated in the drawings) arranged inside a sheath that is the outermost layer of the transmission cable 8. The plural electric wirings are electric wirings for respectively transmitting the imaging signal output from the camera head 9, a control signal output from the control device 5, a synchronization signal, a clock, and power, to the camera head 9.

The display device 4 displays thereon, under control by the control device 5, an image generated by the control device 5. For easy acquisition of a sense of immersion at the time of observation, a display section of the display device 4 is preferably 55 inches or larger, but the display section is not limited to this example.

The control device 5 processes the imaging signal input via the transmission cable 8 from the camera head 9, outputs an image signal to the display device 4, and integrally controls operation of the camera head 9 and the display device 4. A detailed configuration of the control device 5 will be described later.

Figure 2:
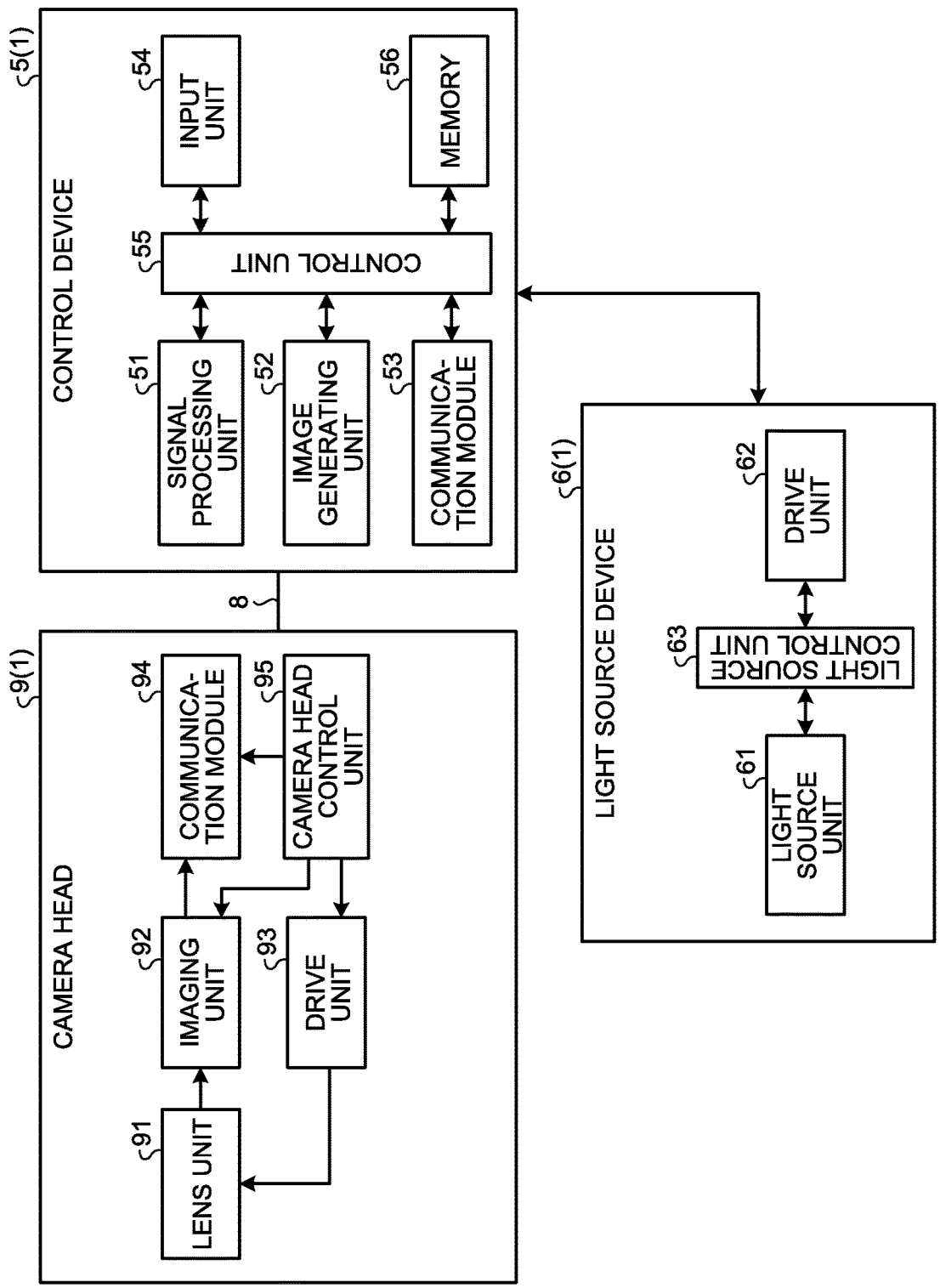
FIG. 2 is a block diagram illustrating a configuration of a camera head, a control device, and a light source device, which are illustrated in FIG. 1.

Described next is a configuration of the camera head 9, the control device 5, and the light source device 6. FIG. 2 is a block diagram illustrating a configuration of the camera head 9, the control device 5, and the light source device 6. In FIG. 2, illustration of a connector that allows the camera head 9 and the transmission cable 8 to be attachable and detachable to and from each other has been omitted.

Hereinafter, a configuration of the control device 5, a configuration of the light source device 6, and a configuration of the camera head 9 will be described in this sequence. Mainly described below are main parts of the present invention, the main parts serving as the configuration of the control device 5. The control device 5 includes, as illustrated in FIG. 2, a signal processing unit 51, an image generating unit 52, a communication module 53, an input unit 54, a control unit 55, and a memory 56. The control device 5 may have, provided therein, a power source unit (not illustrated in the drawings) or the like that generates power source voltage for driving the control device 5 and camera head 9, supplies the power source voltage to each unit of the control device 5, and supplies the power source voltage to the camera head 9 via the transmission cable 8.

The signal processing unit 51 outputs a digitized imaging signal (a pulse signal) to the image generating unit 52 by performing noise removal and, as necessary, signal processing, such as A/D conversion, on the imaging signal output by the camera head 9.

Furthermore, the signal processing unit 51 generates a synchronization signal and a clock for the imaging device 3 and control device 5. The synchronization signal (for example, a synchronization signal for instructing imaging timings of the camera head 9) and the clock (for example, a clock for serial communication) for the imaging device 3 are transmitted to the imaging device 3 through a line not illustrated in the drawings, and the imaging device 3 is driven based on these synchronization signal and clock.

Based on the imaging signal input from the signal processing unit 51, the image generating unit 52 generates an image signal for display to be displayed by the display device 4. The image generating unit 52 generates an image signal for display including a subject image, by executing predetermined signal processing on the imaging signal. Examples of image processing include: interpolation processing; and various types of image processing, such as color correction processing, color enhancement processing, and contour enhancement processing. The image generating unit 52 outputs the generated image signal, to the display device 4.

The communication module 53 output signals from the control device 5 to the imaging device 3, the signals including a later described control signal transmitted from the control unit 55. Furthermore, signals from the imaging device 3 are output to the control device 5. That is, the communication module 53 is a relay device that, collectively outputs signals from the respective units of the control device 5 to be output to the imaging device 3 by, for example, parallel-serial conversion, and allocatively outputs a signal input from the imaging device 3 to the respective units of the control device 5 by, for example, serial-parallel conversion.

The input unit 54 is realized by use of a user interface, such as a keyboard, a mouse, a touch panel, or the like, and receives input of various types of information.

The control unit 55 controls driving of components including the control device 5, the light source device 6, and the camera head 9, and controls input and output of information to and from these components. The control unit 55 generates a control signal by referring to communication information data (for example, communication format information) recorded in the memory 56, and transmits the generated control signal to the imaging device 3 via the communication module 53. Furthermore, the control unit 55 outputs a control signal related to control of the illumination light, to the light source device 6.

The memory 56 is realized by use of a semiconductor memory, such as a flash memory or a dynamic random access memory (DRAM), and has communication information data (for example, communication format information) recorded therein. The memory 56 may have, recorded therein, various programs and the like executed by the control unit 55.

The signal processing unit 51 may have: an AF processing unit that outputs, based on input imaging signals of frames, a predetermined AF evaluation value of each frame; and an AF arithmetic unit that performs AF arithmetic processing for selecting, from the AF evaluation values of the frames from the AF processing unit, a frame, a focus lens position, or the like that is most suitable as a focusing position.

The above described signal processing unit 51, image generating unit 52, communication module 53 and control unit 55 are realized by use of: a general-purpose processor, such as a central processing unit (CPU) having an internal memory (not illustrated in the drawings) with a program recorded therein; or special-purpose processors, such as various arithmetic circuits that execute specific functions, like application specific integrated circuits (ASICs). Furthermore, they may be formed by use of a field programmable gate array (FPGA: not illustrated in the drawings) that is one type of programmable integrated circuits. If they are formed by use of an FPGA, a memory having configuration data stored therein may be provided, and the FPGA, which is a programmable integrated circuit, may be configured according to the configuration data read from the memory.

Described mainly next are main parts of the present invention, the main parts serving as the configuration of the light source device 6. The light source device 6 includes, as illustrated in FIG. 2, a light source unit 61, a drive unit 62, and a light source control unit 63.

Under control by the light source control unit 63, the light source unit 61 emits white light including light of red, green, and blue wavelength bands. Specifically, the light source unit 61 has, for example, a blue light source that emits light of the blue wavelength band, a green light source that emits light of the green wavelength band, and a red light source that emits light of the red wavelength band. Illumination light generated by the light source unit 61 is output to the light guide 7. The light source unit 61 is realized by use of an LED, or a light source that generates white light, such as a xenon lamp or a laser. As to the blue, green, and red wavelength bands, for example, the blue wavelength band is 380 nm to 500 nm, the green wavelength band is 480 nm to 600 nm, and the red wavelength band is 580 nm to 650 nm. Hereinafter, according to the first embodiment, green will be described as a first color, and blue and red will be described as second colors.

The light source unit 61 may have a white light source, a transmissive wavelength band may be selected from white light emitted by the white light source, and light of the selected wavelength band may be caused to enter the light guide 7. In this case, the light source unit 61 is realized by use of, for example, a rotary filter provided with plural filters that are able to be arranged on an optical path of the emitted white light, and the wavelength band of light caused to enter the light guide 7 is able to be changed by switching the filter arranged on the optical path to another filter by rotating the rotary filter under control by the light source control unit 63. This rotary filter selectively transmits therethrough light of the blue green, and red wavelength bands. For example, one filter transmits therethrough light of the green and red wavelength bands, and another filter transmits therethrough light of the green and blue wavelength bands. Of course, a filter that transmits therethrough the light (of the wavelength band of 400 nm to 700 nm) emitted by the light source unit 61 as is may be provided.

The drive unit 62 is formed by use of a motor or the like, and performs, for example, rotary driving for turning on and off the light sources of the color components included in the light source unit 61.

Under control by the control device 5, the light source control unit 63 controls the type (the wavelength band) of the illumination light emitted by the light source device 6 by on-off controlling the light sources of the color components by controlling the light source unit 61. If the light source control unit 63 changes the wavelength band of emitted light by use of the rotary filter, the light source control unit 63 controls the rotary filter through the drive unit 62.

Described mainly next are main parts of the present invention, the main parts serving as the configuration of the camera head 9. The camera head 9 includes, as illustrated in FIG. 2, a lens unit 91, an imaging unit 92, a drive unit 93, a communication module 94 and a camera head control unit 95.

The lens unit 91 is formed by use of one or plural lenses, and forms a subject image condensed by the endoscope 2 onto an imaging surface of an imaging element forming the imaging unit 92. The one or plural lenses are configured to be movable along an optical axis. Provided in the lens unit 91 are: an optical zoom mechanism (not illustrated in the drawings) that changes the angle of view by moving the one or plural lenses; and a focus mechanism that changes the focal point. In addition to the optical zoom mechanism and the focus mechanism, the lens unit 91 may have, provided therein, an aperture mechanism, or an optical filter (for example, a filter that cuts infra-red light) that is insertable into and removable from the optical axis.

Under control by the camera head control unit 95, the imaging unit 92 outputs an imaging signal (an image signal) acquired by capturing an image of a subject, to the communication module 94. This imaging unit 92 is formed by use of: two imaging elements that each have plural pixels arranged in a matrix, receive a subject image formed by the lens unit 91, convert the subject image into an electric signal, and are monochrome; and a prism that spectrally separates observation light and causes the spectrally separated light to be respectively incident on the two imaging elements. The monochrome imaging elements referred to herein mean imaging elements having sensitivity to light of all wavelength bands of the illumination light emitted by the light source device 6. The imaging elements are each realized by use of a complementary metal oxide semiconductor (CMOS), and is a filterless imaging device without a filter that transmits therethrough a specific wavelength only. If the imaging elements are CMOSs, for example, a signal processing unit that performs signal processing (such as A/D conversion) on an electric signal (analog) converted into the electric signal from light and outputs an imaging signal is included in the imaging elements. Targets of "filterless" according to this embodiment do not include an infra-red ray cut filter aimed for shielding of light of a wavelength band not used in generation of an image, such as for cutting of noise. Furthermore, the imaging elements may each be formed of a charge coupled device (CCD). If the imaging elements are each formed of a CCD, for example, a signal processing unit (not illustrated in the drawings) that performs signal processing (such as A/D conversion) on an electric signal (an analog signal) from the imaging elements and outputs an imaging signal is mounted on a sensor chip or the like. A configuration of the imaging unit 92 will be described later.

Figure 3:
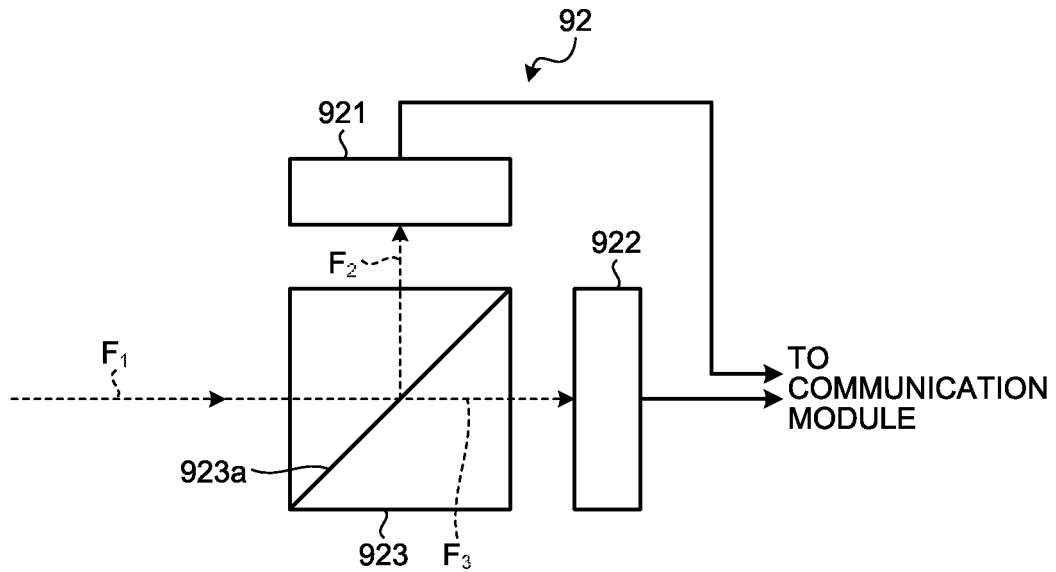
FIG. 3 is a schematic diagram illustrating a configuration of an imaging unit according to the first embodiment of the present invention.

FIG. 3 is a schematic diagram illustrating the configuration of the imaging unit 92. The imaging unit 92 has, as illustrated in FIG. 3, a first imaging element 921, a second imaging element 922, and a prism 923. In the imaging unit 92, observation light from the outside enters the prism 923 via the lens unit 91, and light spectrally separated by the prism 923 enters the first imaging element 921 and second imaging element 922.

The prism 923 has a cubic shape formed of two triangular prism-shaped prisms stuck together, and a thin dichroic film 923a is provided between stuck surfaces thereof. The dichroic film 923a reflects first light including the green wavelength band, and transmits therethrough second light including the blue and red wavelength bands. Therefore, observation light $F_1$ incident on the prism 923 is spectrally separated into first light $F_2$ including light of the green wavelength band and second light $F_3$ including light of the red and blue wavelength bands, and the spectrally separated light beams (the first light $F_2$ and second light $F_3$) are respectively output outside from different outer surfaces (planes) of the prism 923. The prism 923 spectrally disperse the observation light $F_1$ into the first light $F_2$ and second light $F_3$ by one-time reflection, and transmission. According to this first embodiment, the first light $F_2$ including the green wavelength band enters the first imaging element 921, and the second light $F_3$ including the red and blue wavelength bands enters the second imaging element 922. The prism 923 may be any cubic, cuboidal, or polygonal prism, which is able to spectrally separate light incident thereon and to output the spectrally separated light.

Human eyes have a visibility characteristic of sensing green light brightly. According to this embodiment for acquisition of an image sensed brightly by a human with color balance (color reproducibility) among red (R), green (G), and blue (B) maintained, a configuration where the first imaging element 921 outputs a green imaging signal and the second imaging element 922 outputs red and blue imaging signals is adopted.

The drive unit 93 has a driver that causes, under control by the camera head control unit 95, the optical zoom mechanism and the focus mechanism to operate and change the angle of view and focal position of the lens unit 91.

The communication module 94 outputs a signal transmitted from the control device 5 to each unit in the camera head 9, such as the camera head control unit 95. Furthermore, the communication module 94 converts information related to the current state of the camera head 9, into a signal format according to a predetermined transmission scheme, and outputs the converted signal to the control device 5 via the transmission cable 8. That is the communication module 94 is a relay device that allocatively outputs a signal input from the control device 5 and the transmission cable 8 to each unit of the camera head 9 through, for example, serial-parallel conversion or the like, and collectively outputs signals from the respective units of the camera head 9 to be output to the control device 5 and transmission cable 8 through, for example, parallel-serial conversion or the like.

The camera head control unit 95 controls operation of the whole camera head 9 according to: a drive signal input via the transmission cable 8; an instruction signal output from an operating unit, such as a switch, provided exposed on an outer surface of the camera head 9, by a user operation on the operating unit; and the like. Furthermore, the camera head control unit 95 outputs information related to the current state of the camera head 9, to the control device 5 via the transmission cable 8.

The above described drive unit 93, communication module 94, and camera head control unit 95 are realized by use of: a general-purpose processor, such as a central processing unit (CPU) having an internal memory (not illustrated in the drawings) with a program recorded therein; or special-purpose processors, such as various arithmetic circuits that execute specific functions, like application specific integrated circuits (ASICs). Furthermore, they may be formed by use of an FPGA that is one type of programmable integrated circuits. If they are formed of an FPGA, a memory having configuration data stored therein may be provided, and the FPGA, which is a programmable integrated circuit, may be configured according to the configuration data read from the memory.

The camera head 9 or the transmission cable 8 may have, formed therein, a signal processing unit that performs signal processing on an imaging signal generated by the communication module 94 or the imaging unit 92. Furthermore, an imaging clock for driving the imaging unit 92 and a drive clock for driving the drive unit 93 may be generated and output respectively to the imaging unit 92 and the drive unit 93, based on a reference clock generated by an oscillator (not illustrated in the drawings) provided inside the camera head 9; or timing signals for various types of processing in the imaging unit 92, the drive unit 93, and the camera head control unit 95 may be generated and output respectively to the imaging unit 92, the drive unit 93, and the camera head control unit 95, based on a synchronization signal input from the control device 5 via the transmission cable 8. Furthermore, the camera head control unit 95 may be provided in the transmission cable 8 or the control device 5, instead of in the camera head 9.

Figure 4:
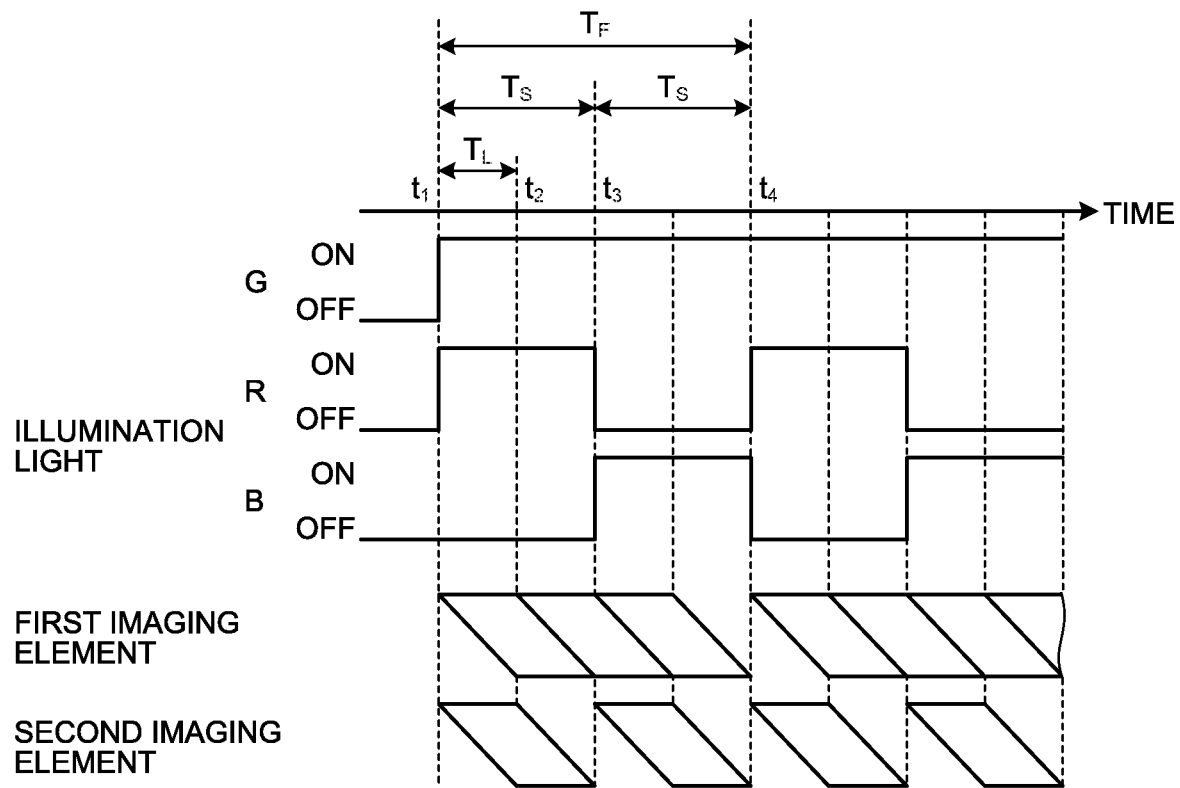
FIG. 4 is a diagram illustrating illumination timings in the endoscope apparatus according to the first embodiment of the present invention.

Illumination timings of the illumination light emitted by the light source device 6 will be described next by reference to FIG. 4. FIG. 4 is a diagram illustrating illumination timings in the endoscope apparatus according to the first embodiment of the present invention. According to the description hereinafter, under control by the control unit 55, the light source control unit 63 controls each unit and causes the illumination light to be emitted. Under control by the control unit 55, the imaging unit 92 and the light source device 6 operate in synchronization with each other. Because the first imaging element 921 and the second imaging element 922 are CMOSs, the electric charge is sequentially read per line.

If a time when illumination is started is $t_1$, at this time $t_1$, the light source device 6 firstly turns the green light source (G) on and causes light of the green wavelength band to be emitted, and also turns the red light source (R) on and causes light of the red wavelength band to be emitted. Thereafter, the light source unit 61 emits light of the red wavelength band during a time period from the time $t_1$ to a time $t_3$, the time period corresponding to a total exposure time period $T_S$ for an imaging element to generate one monochrome image. From the time $t_1$ to the time $t_3$, in a second imaging element 992, the light of the red wavelength band is received, the electric charge is accumulated, and reading of the electric charge is performed under control by the camera head control unit 95. An image signal corresponding to a red monochrome image is thereby generated. If an exposure time period $T_L$ (a time period from the time $t_1$ to a time $t_2$) of one line corresponding to a shutter speed of the CMOS imaging elements is 1/120 second, a total exposure time period $T_S$ is 1/60 second. Furthermore, a "monochrome image" referred to herein is an image that is formed of a single color and is generated based on, for example, light of a green wavelength band.

At the time $t_3$, the red light source is turned off, the blue light source (B) is turned on, and light of the blue wavelength band is emitted. When this happens, light of the green wavelength band still continues to be emitted. Thereafter, the light source unit 61 emits light of the blue wavelength band during the total exposure time period $T_S$ from the time $t_3$ to a time $t_4$. From the time $t_3$ to the time $t_4$, in the second imaging element 992, light of the blue wavelength band is received, the electric charge is accumulated, and reading of the electric charge is performed under control by the camera head control unit 95. An image signal corresponding to a blue monochrome image is thereby generated.

During the red total exposure time period $T_S$ from the time $t_1$ to the time $t_3$, and the blue total exposure time period $T_S$ from the time $t_3$ to the time $t_4$, in the first imaging element 921, light of the green wavelength band is received, the electric charge is accumulated, and reading of the electric charge is performed under control by the camera head control unit 95. An image signal corresponding to a green monochrome image is thereby generated. According to this first embodiment, a time period from the time $t_1$ to the time $t_4$ will be referred to as a frame time period $T_F$ (a frame reading time period) for generation of an image of one frame. In this frame time period $T_F$, the first imaging element 921 continuously performs reading according to the total exposure time period $T_S$. Therefore, in the frame time period $T_F$, three green monochrome images are generated, and one each of the monochrome images from the light of the red and blue wavelength bands is generated.

Image signals from the red, blue, and green light and generated in the frame time period $T_F$ are each transmitted to the control device 5, and formed into an image in the control device 5. In this case, there are three green monochrome images in each frame, and a combination of these three monochrome image may be used to form an image, or a preset monochrome image of the three monochrome images, for example, the second monochrome image in the time series, may be used to be formed into an image.

According to the above described first embodiment, the prism 923 spectrally separates light emitted from a subject due to light emitted from the light source device 6 and having a predetermined wavelength band, into wavelength bands according to color components selectively, causes the spectrally separated light to be respectively incident on only two imaging elements that are the first imaging element 921 and the second imaging element 922, and causes light of different wavelength bands to be respectively incident on the imaging elements simultaneously and photoelectrically converted. According to the first embodiment: a high-definition observation image acquired by plural imaging elements as conventionally done is able to be acquired; downsizing is enabled as compared to a configuration where plural imaging elements (three imaging elements corresponding to red, green, and blue) are provided according to color components; and the acquisition time for electric signals needed for one image to be generated is able to be shortened.

Furthermore, according to the above described first embodiment, because spectral separation is performed by one-time reflection, and transmission, by means of the prism 923: the prism 923 is able to be structured simply and downsized as compared to a prism that emits light to the outside, the light having been spectrally separated by being returned a plural number of times; and as a result, the whole apparatus is able to be decreased in size and weight.

According to the above description of the first embodiment, in the frame time period $T_F$, the first imaging element 921 continuously performs reading according to the total exposure time period $T_S$ and generates three monochrome images, but the frame time period $T_F$ may be an exposure time period of the first imaging element 921, the electric charge accumulated in this frame time period $T_F$ may be read, and one monochrome image may be acquired in this frame time period $T_F$.

Second Embodiment

Described next is a second embodiment of the present invention. A configuration of an endoscope apparatus according to the second embodiment is the same as the above described configuration of the endoscope apparatus 1. The second embodiment is different from the first embodiment in that the light source device 6 further emits illumination light of narrow bands having center wavelengths at wavelengths of 415 nm and 540 nm, and that the endoscope apparatus 1 enables special light observation for observation of states of blood vessels of a mucous membrane surface layer and a layer deeper than the mucous membrane surface layer by use of difference in absorption of hemoglobin by light of each wavelength. According to this second embodiment, due to control by the control unit 55, switch-over is enabled between: a normal observation mode where an image based on light of red, green, and blue wavelength bands is generated; and a special observation mode where an image based on light of green and blue narrow bands is generated. Special light observation by means of illumination light of narrow bands having center wavelengths of wavelengths 415 nm and 540 nm is generally called narrow band imaging (NBI) observation. According to this second embodiment, the light source device 6 further has a blue narrow band light source that emits light of 390 nm to 445 nm and a green narrow band light source that emits light of 530 nm to 550 nm.

Figure 5:
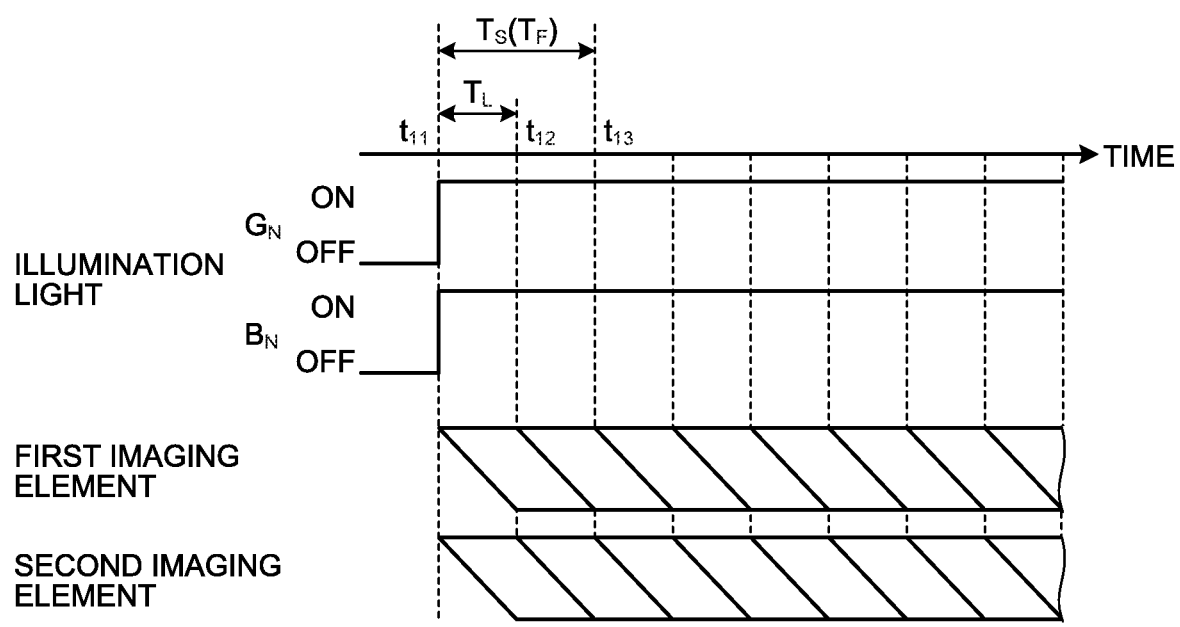
FIG. 5 is a diagram illustrating illumination timings for a special observation mode in an endoscope apparatus according to a second embodiment of the present invention.

FIG. 5 is a diagram illustrating illumination timings of the special observation mode in the endoscope apparatus according to the second embodiment of the present invention. If a time when illumination is started is $t_{11}$, at this time $t_{11}$, the light source device 6 firstly turns the green narrow band light source ($G_N$) on and emits light of a green narrow band, and also turns the blue narrow band light source ($B_N$) on and emits light of a blue narrow band. From the time $t_{11}$ to a time $t_{13}$, in the first imaging element 921, light of the green narrow band is received, the electric charge is accumulated, and reading of the electric charge is performed under control by the camera head control unit 95. An image signal corresponding to a green narrow band monochrome image is thereby generated. From the time $t_{11}$ to the time $t_{13}$, in the second imaging element 922 on the other hand, light of the blue narrow band is received, the electric charge is accumulated, and reading of the electric charge is performed under control by the camera head control unit 95. An image signal corresponding to a blue narrow band monochrome image is thereby generated. Similarly to the first embodiment, if the exposure time period $T_L$ (a time period from the time $t_{11}$ to a time $t_{12}$) of the CMOS imaging elements is 1/120 second, the total exposure time period $T_S$ is 1/60 second.

From the time $t_{13}$, the first imaging element 921 and second imaging element 922 repeat the reading processing per line. According to this second embodiment, in the total exposure time period $T_S$ from the time $t_{11}$ to the time $t_{13}$, an image signal from light of the green narrow band and an image signal from light of the blue narrow band are simultaneously generated. Therefore, the total exposure time period $T_S$ and a frame time period for generation of one image (the above described frame time period $T_F$) are the same. Accordingly, in the frame time period $T_F$, one narrow band monochrome image from the light of the green narrow band is generated, and one narrow band monochrome image from the light of the blue narrow band is generated.

The illumination timings in the normal observation mode are similar to those according to the above described first embodiment.

Image signals generated from the light of the blue and green narrow bands are each transmitted to the control device 5, and formed into an image in the control device 5.

According to the above described second embodiment, the prism 923 spectrally separates light emitted from a subject due to light emitted from the light source device 6 and having a predetermined wavelength band, into wavelength bands according to color components selectively, causes the spectrally separated light to be respectively incident on only two imaging elements that are the first imaging element 921 and the second imaging element 922, and causes the light of the different wavelength bands to be simultaneously incident on the imaging elements and photoelectrically converted. According to the second embodiment, a high-definition observation image acquired by plural imaging elements as conventionally done is able to be acquired, and the acquisition time for electric signals needed for one image to be generated is able to be shortened.

Furthermore, according to the second embodiment, due to the configuration, in which the mode where an image based on light of the red, green, and blue wavelength bands is generated and the mode where an image based on light of the green and blue narrow bands is generated are selectable, downsizing is enabled as compared to a configuration where plural imaging elements (three imaging elements corresponding to red, green, and blue) are provided according to color components.

Third Embodiment

Described next is a third embodiment of the present invention. A configuration of an endoscope apparatus according to the third embodiment is the same as the above described configuration of the endoscope apparatus 1. The third embodiment is different from the first embodiment in that the light source device 6 further emits near infra-red light having a center wavelength of 805 nm and a center wavelength of 940 nm, and that the endoscope apparatus 1 enables special light observation for observation of shadow of blood vessel parts of submucosal layers due to absorption of indocyanine green (ICG) having an absorption peak in near infra-red light around the wavelength of 805 nm in blood. According to this third embodiment, due to control by the control unit 55, switch-over is possible between: a normal observation mode where an image based on light of red, green, and blue wavelength bands is generated; and a special observation mode where an image based on near infra-red light is generated. Special light observation by means of the near infra-red light having the center wavelength of 805 nm and the center wavelength of 940 nm is generally called infra-red imaging (IRI) observation. IRI observation enables observation by means of near infra-red light by intravenous injection of an agent called indocyanine green (ICG) into a subject, the agent serving as a contrast agent. According to this third embodiment, the light source device 6 further has a near infra-red light source that emits light of 790 nm to 820 nm and 905 nm to 970 nm.

Figures 6, 7:
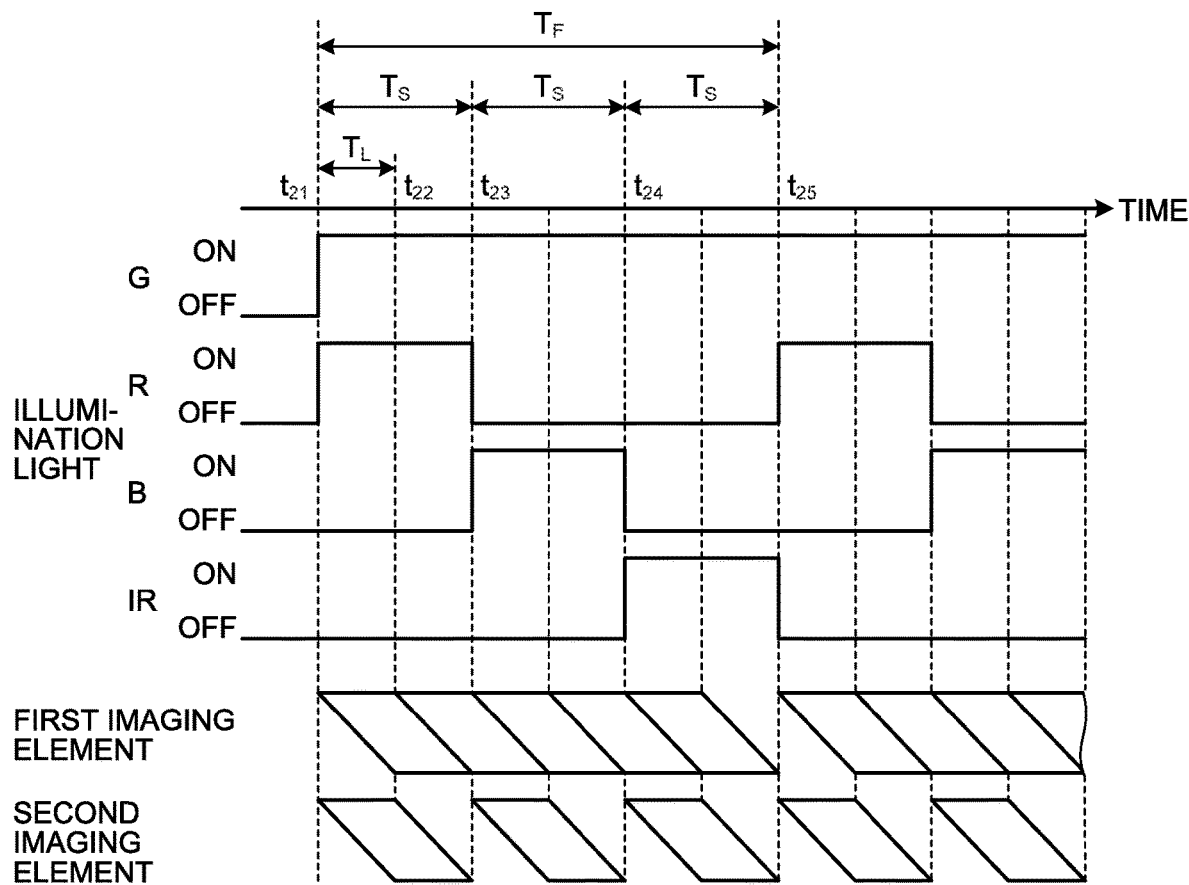
FIG. 6 is a diagram illustrating illumination timings for a special observation mode in an endoscope apparatus according to a third embodiment of the present invention.
FIG. 7 is a schematic diagram illustrating a configuration of pixels of an imaging element of an imaging unit according to a fourth embodiment of the present invention.

FIG. 6 is a diagram illustrating illumination timings in the special observation mode in the endoscope apparatus according to the third embodiment of the present invention. If a time when illumination is started is $t_{21}$, at this time $t_{21}$, the light source device 6 firstly turns the green light source (G) on and emits light of the green wavelength band, and also turns the red light source (R) on and emits light of the red wavelength band. Thereafter, the light source unit 61 emits light of the red wavelength band in the total exposure time period $T_S$ from the time $t_{21}$ to a time $t_{23}$. From the time $t_{21}$ to the time $t_{23}$, in the second imaging element 922, the light of the red wavelength band is received, the electric charge is accumulated, and reading of the electric charge is performed under control by the camera head control unit 95. An image signal corresponding to a red monochrome image is thereby generated. Similarly to the above described first embodiment, if the exposure time period $T_L$ (a time period from the time $t_{21}$ to a time $t_{22}$) of the CMOS imaging elements is 1/120 second, the total exposure time period $T_S$ is 1/60 second.

At the time $t_{23}$, the red light source is turned off, the blue light source (B) is turned on, and light of the blue wavelength band is emitted. When this happens, light of the green wavelength band still continues to be emitted. Thereafter, the light source unit 61 emits light of the blue wavelength band in the total exposure time period $T_S$ from the time $t_{23}$ to a time $t_{24}$. From the time $t_{23}$ to the time $t_{24}$, in the second imaging element 922, light of the blue wavelength band is received, the electric charge is accumulated, and reading of the electric charge is performed under control by the camera head control unit 95. An image signal corresponding to a blue monochrome image is thereby generated.

Furthermore, at the time $t_{24}$, the blue light source is turned off, the near infra-red light source (IR) is turned on, and near infra-red light is emitted. When this happens also, light of the green wavelength band still continues to be emitted. Thereafter, the light source unit 61 emits near infra-red light in the total exposure time period $T_S$ from the time $t_{24}$ to a time $t_{25}$. From the time $t_{24}$ to the time $t_{25}$, in the second imaging element 922, the near infra-red light is received, the electric charge is accumulated, and reading of the electric charge is performed under control by the camera head control unit 95. An image signal corresponding to a near infra-red monochrome image is thereby generated.

In the red total exposure time period $T_S$ from the time $t_{21}$ to the time $t_{23}$, the blue exposure time period $T_S$ from the time $t_{23}$ to the time $t_{24}$, and the near infra-red light total exposure time period $T_S$ from the time $t_{24}$ to the time $t_{25}$, in the first imaging element 921, light of the green wavelength band is received, light of the green wavelength band is received, the electric charge is accumulated, and reading of the electric charge is performed under control by the camera head control unit 95. An image signal corresponding to a green monochrome image is thereby generated. According to this third embodiment, a time period from the time $t_{21}$ to the time $t_{25}$ will be referred to as the frame time period $T_F$ for generation of an image of one frame. In this frame time period $T_F$, the first imaging element 921 continuously read lines according to the total exposure time period $T_S$. Therefore, in the frame time period $T_F$, five green monochrome images are generated, and one each of red and blue monochrome images and one near infra-red light monochrome image are generated.

Image signals generated in the frame time period $T_F$ from the light of the red, blue, and green wavelength bands and the near infra-red light are each transmitted to the control device 5, and formed into an image in the control device 5. A preset color, for example, is arranged in the image from the near infra-red light. Brightness of the image from the near infra-red light may be changed according to luminance.

According to the above described third embodiment, the prism 923 spectrally separates light emitted from a subject due to light emitted from the light source device 6 and having a predetermined wavelength band, into wavelength bands according to color components selectively, causes the spectrally separated light to be respectively incident on only two imaging elements that are the first imaging element 921 and the second imaging element 922, and causes light of different wavelength bands to be respectively incident on the imaging elements simultaneously and photoelectrically converted. According to the third embodiment: a high-definition observation image acquired by plural imaging elements as conventionally done is able to be acquired; downsizing is enabled as compared to a configuration where plural imaging elements (four imaging elements corresponding to red, green, and blue light and near infra-red light) are provided according to color components; and the acquisition time for electric signals needed for one image to be generated is able to be shortened.

This third embodiment may be combined with the above described first and second embodiments into a configuration where switch-over between the normal observation and the IRI observation is performed, or switch-over among the normal observation, the NBI observation, and the IRI observation is performed.

Fourth Embodiment

Described next is a fourth embodiment of the present invention. A configuration of an endoscope apparatus according to the fourth embodiment is the same as the above described configuration of the endoscope apparatus 1. According to the fourth embodiment, positions of the first imaging element 921 and the second imaging element 922 have been displaced from each other, the positions being relative to observation light (the above described observation light $F_1$).

FIG. 7 is a schematic diagram illustrating a configuration of pixels of an imaging element of the imaging unit 92 according to the fourth embodiment. Hereinafter, the pixel configuration of the first imaging element 921 will be described by use of FIG. 7, but the same applies to the second imaging element 922, and arrangement of pixels of the second imaging element 922 is the same as arrangement of the pixels of the first imaging element 921. The first imaging element 921 has plural pixels that receive light from the lens unit 91 and the prism 923, the plural pixels being two-dimensionally arranged in a square array (arranged in a matrix). By photoelectrically converting light received by each of the pixels, the first imaging element 921 generates an electric signal. The electric signal includes a pixel value (a luminance value) of each of the pixels and positional information of the pixels. In FIG. 7, a pixel $P_{xy}$ (where x and y are natural numbers) denotes a pixel arranged at a row x and a column y.

The first imaging element 921 and the second imaging element 922 each has a light receiving surface where the pixels receive light, the light receiving surface being arranged at a position conjugate to a focal plane of the lens unit 91, and the position of the pixel $P_{xy}$ of the first imaging element 921 and the position of the pixel $P_{xy}$ of the second imaging element 922 are displaced from each other with respect to an optical axis of the observation light $F_1$ by ½ pixel each in a row direction and a column direction that are array directions of the pixel array. For example, if the first imaging element 921 and the second imaging element 922 are superimposed on each other with the optical axes of the observation light $F_1$ aligned with each other, the position of a pixel $P_{11}$ of the second imaging element 922 is displaced from the position of a pixel $P_{11}$ of the first imaging element 921 by ½ pixel each in the row direction and column direction of the array directions of the pixel array of the first imaging element 921. The first imaging element 921 and the second imaging element 922 are fixed by a fixing member not illustrated in the drawings, in a state where the optical axis direction of the observation light $F_1$, a yaw direction, a roll direction, a pitch direction, and two axial directions (a horizontal direction and a vertical direction) have been adjusted, the two axial directions being orthogonal to each other on a plane vertical to the optical axis.

Figure 8:
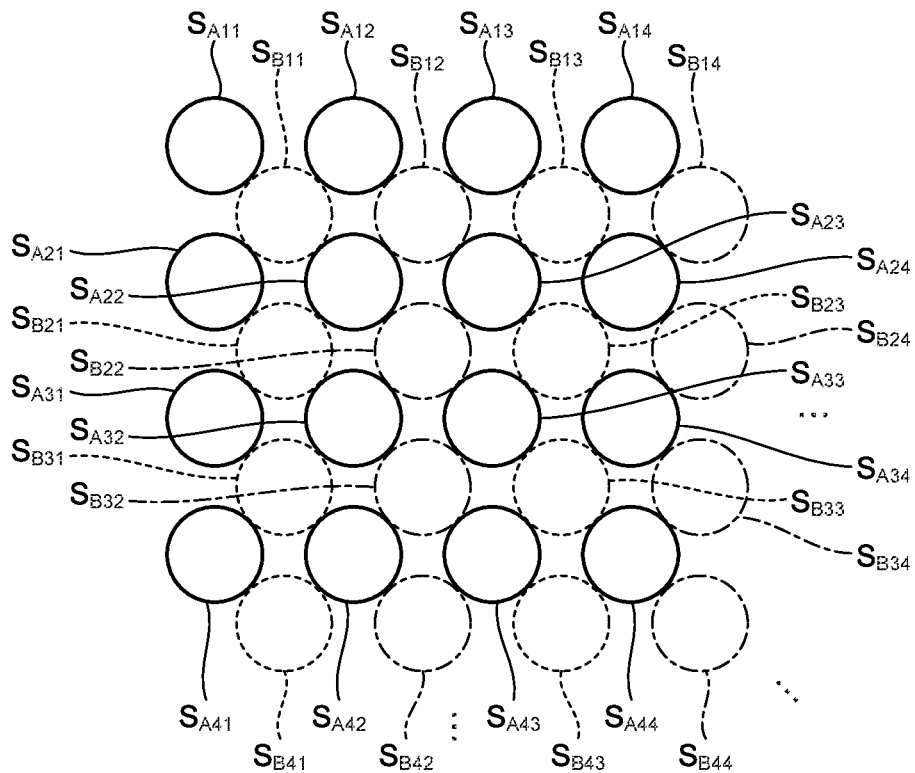
FIG. 8 is a schematic diagram illustrating arrangement of light (spots) acquired by two imaging elements of the imaging unit according to the fourth embodiment of the present invention.

Imaging signals acquired by the first imaging element 921 and the second imaging element 922 will be described next by reference to FIG. 8. FIG. 8 is a schematic diagram illustrating arrangement of light (spots) acquired by the two imaging elements of the imaging unit 92 according to the fourth embodiment. In FIG. 8, light incident on each pixel is schematically illustrated as a circle (a spot). For example, light incident on the pixel $P_{11}$ of the first imaging element 921 is illustrated as a spot $S_{A11}$, and light incident on the pixel $P_{11}$ of the second imaging element 922 is illustrated as a spot $S_{B11}$.

Spots received by the pixels of the first imaging element 921 (for example, the spot $S_{A11}$ to a spot $S_{A44}$ illustrated in FIG. 8) are arranged in a matrix. Furthermore, spots received by the pixels of the second imaging element 922 (for example, the spot $S_{B11}$ to a spot $S_{B44}$ illustrated in FIG. 8) are arranged in a matrix.

If the arrangement of the spots received by the pixels of the first imaging element 921 and the arrangement of the spots received by the pixels of the second imaging element 922 are superimposed on each other with the optical axes of the observation light aligned with each other, the positions of the pixels $P_{xy}$ of the first imaging element 921 and second imaging element 922 are displaced from each other by ½ pixel each in the row direction and column direction, and thus, as illustrated in FIG. 8, the spots $S_{B11}$ to $S_{B44}$ in the second imaging element 922 are arranged between the spots $S_{A11}$ to $S_{A44}$ in the first imaging element 921. In other words, when, for example, the spots $S_{A11}$ to $S_{A44}$ in the first imaging element 921 and the spots $S_{B11}$ to $S_{B44}$ in the second imaging element 922 are viewed along the row direction of the pixels $P_{xy}$, the spots $S_{A11}$ to $S_{A44}$ and the spots $S_{B11}$ to $S_{B44}$ are in a state of being arranged independently from each other.

By displacement of the pixel positions of the first imaging element 921 and second imaging element 922 from each other with respect to the optical axis by ½ pixel each in the row direction and column direction, the number of spots as viewed along any one of the row direction and column direction is able to be doubled if imaging elements having the same number of pixels are used. Therefore, as to the number of pixels of an image signal for display generated by the image generating unit 52, if luminance values of RGB components are given to all of the spots by interpolation of the color components for each spot, the number of pixels in any one of the row direction and column direction is doubled, and the definition is able to be regarded as being doubled. A known method, such as the nearest neighbor method, the bilinear method, or the bicubic method, may be used as interpolation processing.

Specifically, if imaging elements each having the number of pixels according to a standard definition (SD) image signal are used, an image signal is able to be regarded as an image signal corresponding to a high definition (HD) image signal. Furthermore, if imaging elements each having the number of pixels according to an HD image signal are used, an image signal is able to be regarded as an image signal corresponding to a higher definition 4K image signal; and if imaging elements each having the number of pixels according to a 4K image signal are used, an image signal is able to be regarded as an image signal corresponding to an even higher definition 8K image signal. An SD image signal is, for example, an image signal having definition of around 720 in the row direction, and around 480 in the column direction. An HD image signal is, for example, an image signal having definition of around 1920 in the row direction, and around 1080 in the column direction. A 4K image signal is, for example, an image signal having definition of around 3820 in the row direction, and around 2160 in the column direction. An 8K image signal is, for example, an image signal having definition of around 7680 in the row direction, and around 4320 in the column direction.

According to the above described fourth embodiment, the above described effects of the first embodiment are able to be obtained; and because the pixel positions of the first imaging element 921 and second imaging element 922 with respect to the optical axis are displaced from each other by ½ pixel each in the row direction and column direction, a high definition observation image is able to be acquired.

According to the above description of the fourth embodiment, the pixel positions of the first imaging element 921 and second imaging element 922 with respect to the optical axis are displaced from each other by ½ pixel each in the row direction and column direction, but the pixel positions may just be displaced from each other only in a direction where the number of pixels is doubled in the generated image signal. That is, the pixel positions of the first imaging element 921 and second imaging element 922 with respect to the optical axis may just be displaced from each other in a direction where the number of pixels is doubled in the image signal. The pixel positions of the first imaging element 921 and second imaging element 922 with respect to the optical axis may just be displaced from each other in at least one of two directions (the row direction and horizontal direction) that are along array directions of the pixel array.

Fifth Embodiment

Figure 9:
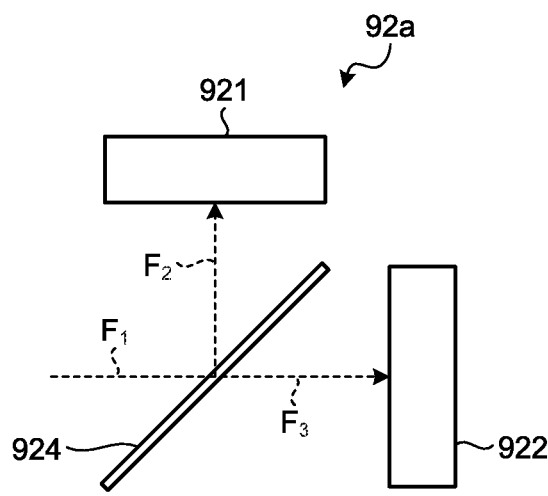
FIG. 9 is a schematic diagram illustrating a configuration of animating unit according to a fifth embodiment of the present invention.

Described next is a fifth embodiment of the present invention. FIG. 9 is a schematic diagram illustrating a configuration of an imaging unit 92a according to the fifth embodiment, of the present invention. According to the above description of the first embodiment, spectral separation is performed by use of the prism 923, but in this modified example, spectral separation is performed by use of a thin film mirror 924 that is provided with a dichroic film and is plate-shaped.

The imaging unit 92a according to this fifth embodiment has the first imaging element 921, the second imaging element 922, and the thin film mirror 924. In the imaging unit 92a, the observation light $F_1$ from the outside enters the thin film mirror 924 via the lens unit 91, and light beams spectrally separated by the thin film mirror 924 enter the first imaging element 921 and second imaging element 922.

The thin film mirror 924 has a plate shape provided with the dichroic film on its surface at the lens unit 91 side. Similarly to the above described dichroic film 923a, this dichroic film reflects light of the green wavelength band, and transmits therethrough light of the red and blue wavelength bands. Therefore, the observation light $F_1$ that has entered the thin film mirror 924 is spectrally separated into the first light $F_2$ including the green wavelength band and the second light $F_3$ including the red and blue wavelength bands.

According to this fifth embodiment, because spectral separation is performed by use of the thin film mirror 924 that is plate-shaped, the above described effects of the first embodiment are obtained, and weight reduction is enabled as compared to the case where the prism 923 is used. According to the above description of the modified example, the configuration has the dichroic film provided in a plate-like member serving as the thin film mirror 924, but for further reduction of the influence of degradation in the optical performance due to the thickness of the mirror of the thin film mirror 924, a configuration having, for example, a thin film mirror, such as a pellicle mirror having a thickness equal to or less than 0.1 mm, may be adopted.

Sixth Embodiment

Figure 10:
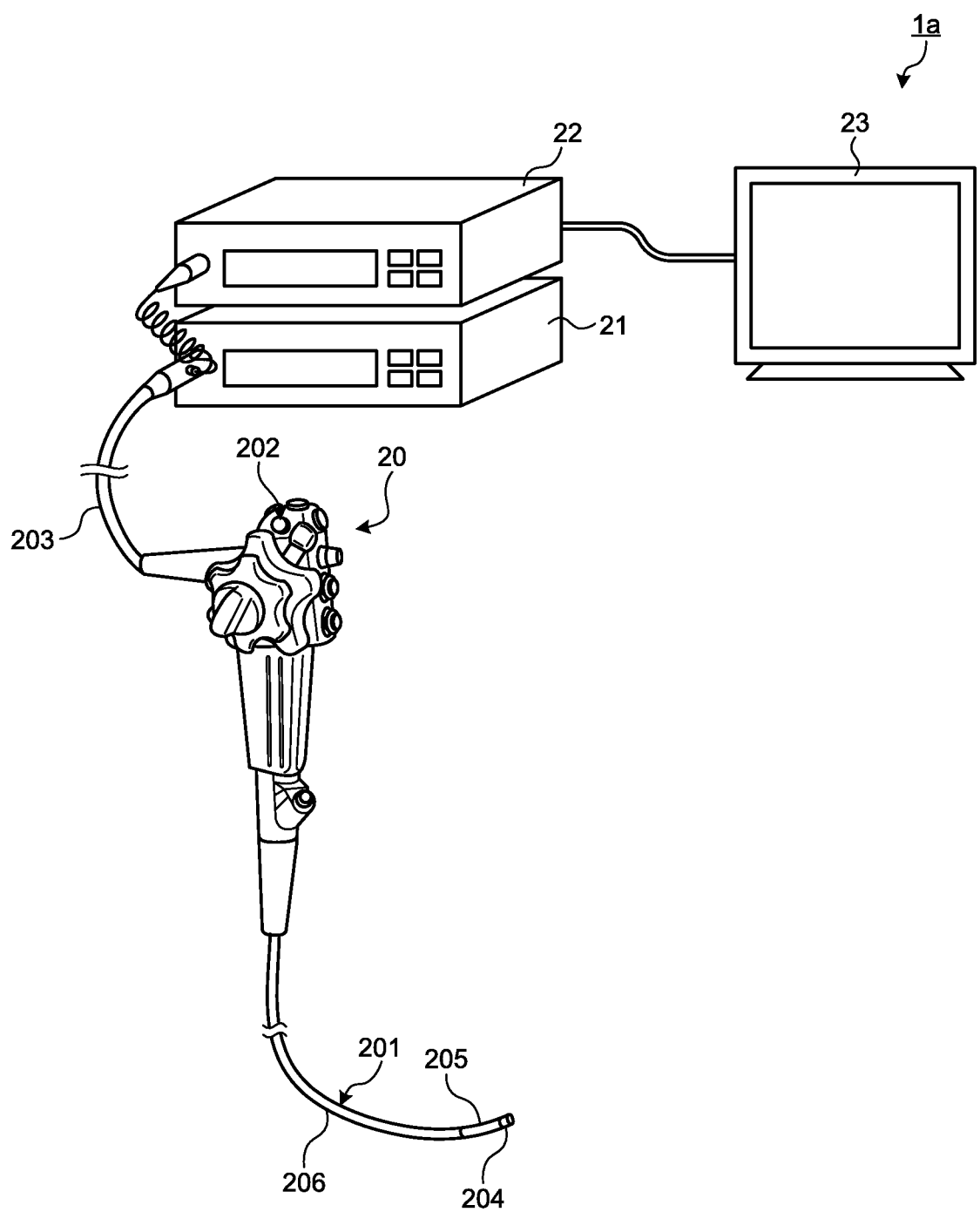
FIG. 10 is a diagram illustrating a schematic configuration of an endoscope apparatus according to a sixth embodiment of the present invention.

Described next is a sixth embodiment of the present invention. FIG. 10 is a diagram illustrating a schematic configuration of an endoscope apparatus 1a according to the sixth embodiment of the present invention. With respect to the above described first embodiment, the endoscope apparatus 1 having a rigid endoscope used therein as the endoscope 2 has been described, but without being limited thereto, an endoscope apparatus having a flexible endoscope used therein as the endoscope 2 may be adopted. Described with respect to this sixth embodiment is an example of a case where an imaging unit is provided at a distal end of an insertion unit of a flexible endoscope.

The endoscope apparatus 1a includes: an endoscope 20 that captures an in-vivo image of an observed region and generates an imaging signal by insertion of an insertion unit 201 into a subject; a light source device 21 that generates illumination light to be emitted from a distal end of the endoscope 20; a control device 22 that performs predetermined image processing on the imaging signal acquired by the endoscope 20 and integrally controls operation of the whole endoscope apparatus 1a; and a display device 23 that displays thereon the in-vivo image that has been subjected to the image processing by the control device 22. The endoscope apparatus 1a acquires an in-vivo image in a subject, such as a patient, by insertion of the insertion unit 201 into the subject. The light source device 21 has the above described functions of the light source device 6. Furthermore, the control device 22 has the above described functions of the signal processing unit 51, the image generating unit 52, and the like.

The endoscope 20 includes: the insertion unit 201 that has flexibility and is elongated; an operating unit 202 that is connected to a proximal end of the insertion unit 201 and receives input of various operation signals; and a universal cord 203 that extends in a direction different from a direction, in which the insertion unit 201 extends from the operating unit 202, and that has various cables built therein, the various cables being connected to the light source device 21 and the control device 22.

The insertion unit 201 has: a distal end portion 204 having, built therein, an imaging unit 92b (see FIG. 11) according to the sixth embodiment; a bending portion 205 that is formed of plural bending pieces and is bendable; and a flexible tube portion 206 that is connected to a proximal end of the bending portion 205, has flexibility, and is long.

Figure 11:
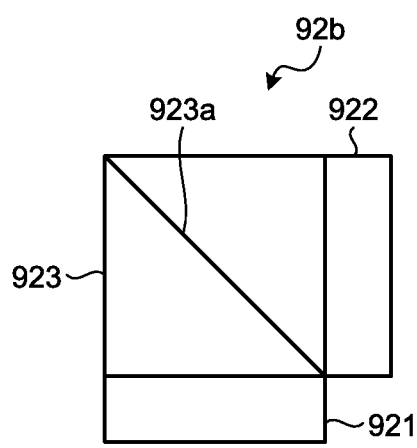
FIG. 11 is a schematic diagram illustrating a configuration of an imaging unit according to the sixth embodiment of the present invention.

FIG. 11 is a schematic diagram illustrating a configuration of the imaging unit 92b according to the sixth embodiment of the present invention. The imaging unit 92b has, similarly to the imaging unit 92, the first imaging element 921, the second imaging element 922, and the prism 923. The imaging unit 92b has, arranged therein, light receiving surfaces of the first imaging element 921 and second imaging element 922, on different surfaces of the prism 923, respectively. The surfaces where the first imaging element 921 and second imaging element 922 are arranged in the prism 923 are preferably surfaces orthogonal to each other.

Furthermore, if a thin film substrate, such as an FPC substrate, is used in electric connection between the first imaging element 921 and second imaging element 922 and the communication module 94 or the like, the imaging unit 92b is able to be made even thinner.

When the imaging unit 92b according to the sixth embodiment is used, even if the imaging unit 92b is provided in the distal end portion 204 of the insertion unit 201 of the flexible endoscope, the insertion unit 201 is prevented from becoming large in diameter.

Modes for implementation of the present invention have been described thus far, but the present invention is not limited only to the above described embodiments. According to the above description of the embodiments, the control device 5 performs the signal processing and the like, but the signal processing and the like may be performed at the camera head 9 side.

With respect to the above described embodiments, the case where the exposure time period $T_L$ of the CMOS imaging elements is, for example, 1/120 second has been described, but without being limited to this case, the exposure time period $T_L$ may be 1/60 second, or the exposure time period $T_L$ of the first imaging element 921, and the exposure time period $T_L$ of the second imaging element 922 may be set to be different time periods.

Furthermore, with respect to the above described embodiments, a camera head (the camera head 9) of a rigid endoscope and a flexible endoscope have been described as examples; and the definition of the imaging elements generally used in these devices is the SD definition (around 720 in the row direction and around 480 in the column direction) for the flexible endoscope and the HD definition (around 1920 in the row direction and around 1080 in the column direction) for the camera head. By adoption of the imaging units according to the embodiments, high quality observation images are ensured with the decrease in size and weight, and the definition of each device is able to be multiplied by about two (for example, the SD to the HD, or the HD to the 4K) by the arrangement through the relative displacement between the pixels of the two imaging elements.

INDUSTRIAL APPLICABILITY

As described above, an endoscope apparatus according to the present invention is useful in acquisition of a high definition observation image with increase in apparatus size prevented.

REFERENCE SIGNS LIST 1, 1a ENDOSCOPE APPARATUS
2, 20 ENDOSCOPE
3 IMAGING DEVICE
4, 23 DISPLAY DEVICE
5, 22 CONTROL DEVICE
6, 21 LIGHT SOURCE DEVICE
7 LIGHT GUIDE
8 TRANSMISSION CABLE
9 CAMERA HEAD
51 SIGNAL PROCESSING UNIT
52 IMAGE GENERATING UNIT
53 COMMUNICATION MODULE
54 INPUT UNIT
55 CONTROL UNIT
56 MEMORY
91 LENS UNIT
92, 92a, 92b IMAGING UNIT
93 DRIVE UNIT
94 COMMUNICATION MODULE
95 CAMERA HEAD CONTROL UNIT
201 INSERTION UNIT
202 OPERATING UNIT
203 UNIVERSAL CORD
204 DISTAL END PORTION
205 BENDING PORTION
206 FLEXIBLE TUBE PORTION
921 FIRST IMAGING DEVICE
922 SECOND IMAGING DEVICE
923 PRISM
924 THIN FILM MIRROR

The invention claimed is:

1. A medical apparatus, comprising:
a light source configured to continuously emit first light of a first wavelength band, and sequentially emit second light of plural second wavelength bands different from the first wavelength band and different from each other, wherein the first wavelength band is between the second wavelength bands; and
a spectrometer configured to:
spectrally separate light from a subject, the light arising from illumination light emitted by the light source, into light of the first wavelength band and light of the second wavelength bands;
generate a first image signal by receiving and photoelectrically converting the light of the first wavelength band; and
generate a second image signal by respectively receiving and photoelectrically converting the light of the second wavelength bands.

2. The medical apparatus according to claim 1, wherein
the light source continuously emits light of a green wavelength band that is the first wavelength band, and sequentially emits light of a red wavelength band and light of a blue wavelength band, the red wavelength band and blue wavelength band being the second wavelength hands, and
the spectrometer is configured to generate the first and second image signals in synchronization with emission time periods of the first and second light output by the light source.

3. The medical apparatus according to claim 2, further comprising circuitry configured to:
control the light source to switch-over between: normal illumination where, in a frame reading time period for reading of a signal corresponding to one frame, the light of the green wavelength band is continuously emitted and the light of the red wavelength band and the light of the blue wavelength band are sequentially emitted; and narrow band illumination where, in the frame reading time period, light of a green narrow band is emitted and light of a blue narrow band is also emitted.

4. The medical apparatus according to claim 2, further comprising circuitry configured to:
in a frame reading time period for reading of a signal corresponding to one frame, control the light source to continuously emit the light of the green wavelength band and sequentially emit the light of the red wavelength hand, the light of the blue wavelength band, and near infra-red light.

5. The medical apparatus according to claim 1, further comprising:
circuitry configured to control generation of the first and second imaging signals and control a wavelength band of light emitted by the light source and emission timings; and
an image sensor to generate an image based on an electric signal generated by the first and second imaging signals.

6. A camera head for a medical apparatus, comprising:
a spectroscope configured to:
spectrally separate light from a subject, the light arising from illumination light emitted by a light source configured to continuously emit first light of a first wavelength band, and sequentially emit second light of plural second wavelength bands different from the first wavelength band and different from each other, wherein the first wavelength band is between the second wavelength bands, into light of the first wavelength band and light of the second wavelength bands;
generate a first image signal by receiving and photoelectrically converting the light of a first wavelength band; and
generate a second image signal by respectively receiving and photoelectrically converting the light of the second wavelength bands.

7. The camera head according to claim 6, wherein the first wavelength hand is a green wavelength band, and the second wavelength bands include a red wavelength band and a blue wavelength band, and
the spectroscope is configured to generate the first and second image signals in synchronization with emission time periods of the first and second light output by the light source.

8. A method, comprising:
continuously emitting first light of a first wavelength band;
sequentially emitting second light of plural second wavelength bands different from the first wavelength band and different from each other, wherein the first wavelength band is between the second wavelength bands;
illuminating a subject using the first light and the second light;
spectrally separating light from the subject
generating a first image signal by receiving and photoelectrically converting the light of the first wavelength band; and
generating a second image signal by respectively receiving and photoelectrically converting the light of the second wavelength bands.

9. The method according to claim 8, wherein
the first wavelength band is a green wavelength band, the second wavelength bands include a red wavelength hand and a blue wavelength band, and the first and second image signals is in synchronization with emission time periods of the first and second light.

10. The method according to claim 8, further comprising switching between normal illumination where, in a frame reading time period for reading of a signal corresponding to one frame, the light of the green wavelength band is continuously emitted and the light of the red wavelength band and the light of the blue wavelength band are sequentially emitted; and narrow band illumination where, in the frame reading time period, light of a green narrow band is emitted and light of a blue narrow band is also emitted.

11. The method according to claim 8, wherein in a frame reading time period for reading of a signal corresponding to one frame, continuously emitting the light of the green wavelength band and sequentially emitting the light of the red wavelength band, the light of the blue wavelength band, and near infra-red light.

12. The method according to claim 8, wherein further comprising:

controlling generation of the first and second imaging signals and a wavelength band of light emitted and emission timings; and generating an image based on an electric signal generated by the first and second imaging signals.

* * * * *